United States Patent
Hu

(10) Patent No.: US 11,076,980 B2
(45) Date of Patent: Aug. 3, 2021

(54) MENSTRUAL FLUID COLLECTION DEVICE AND METHOD THEREOF

(71) Applicant: Kate Hu, Bethesda, MD (US)

(72) Inventor: Kate Hu, Bethesda, MD (US)

(*) Notice: Subject to any disclaimer, the term of this patent is extended or adjusted under 35 U.S.C. 154(b) by 629 days.

(21) Appl. No.: 15/704,347

(22) Filed: Sep. 14, 2017

(65) Prior Publication Data

US 2019/0125571 A1 May 2, 2019

Related U.S. Application Data

(60) Provisional application No. 62/394,730, filed on Sep. 14, 2016.

(51) Int. Cl.
| | | |
|---|---|---|
| *A61F 13/00* | (2006.01) | |
| *A61F 5/455* | (2006.01) | |
| *A61F 13/02* | (2006.01) | |
| *A61M 35/00* | (2006.01) | |
| *A61M 1/00* | (2006.01) | |
| *A61M 3/00* | (2006.01) | |
| *A61M 31/00* | (2006.01) | |

(52) U.S. Cl.
CPC .................. *A61F 5/4553* (2013.01)

(58) Field of Classification Search
CPC .. A61F 5/45; A61F 13/00; A61F 13/02; A61F 8/44; A61M 35/00; A61M 1/00; A61M 3/00; A61M 31/00
See application file for complete search history.

(56) References Cited

U.S. PATENT DOCUMENTS

| | | | | |
|---|---|---|---|---|
| 3,157,180 A * | 11/1964 | Bakunin | ............... | A61F 5/4553 604/330 |
| 3,841,333 A * | 10/1974 | Zalucki | ................. | A61F 5/4553 604/330 |
| 6,746,432 B2 * | 6/2004 | Zadini | .............. | A61B 17/12099 604/330 |
| 2008/0077097 A1 * | 3/2008 | Chambers | ............. | A61F 5/4553 604/330 |

* cited by examiner

*Primary Examiner* — Tatyana Zalukaeva
*Assistant Examiner* — Ilya Y Treyger
(74) *Attorney, Agent, or Firm* — Law Office of Jerry Joseph, PLC; Jerry K. Joseph

(57) ABSTRACT

A menstrual fluid collection device including a flexible container having a storage cavity to store a fluid and a movable opening formed in a closed position at a first end of the flexible container, the storage cavity to receive the fluid when the movable opening is in an open position and an inflatable seal member coupled to and extending around the flexible container, the inflatable seal member configured to move the opening to the open position, when inflated.

14 Claims, 16 Drawing Sheets

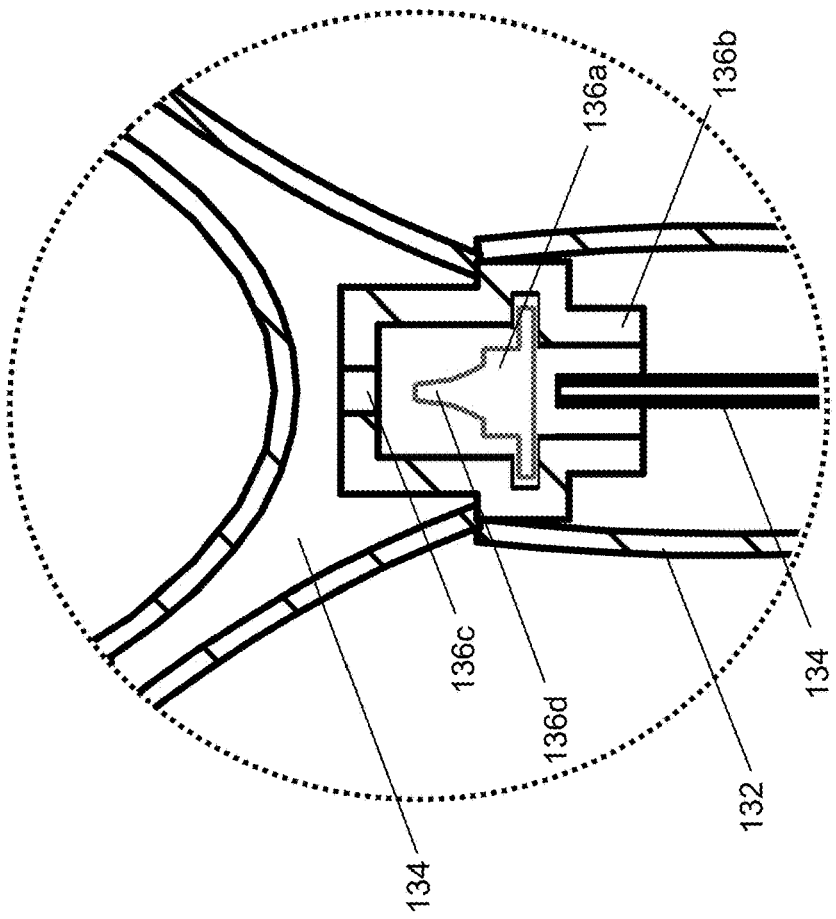
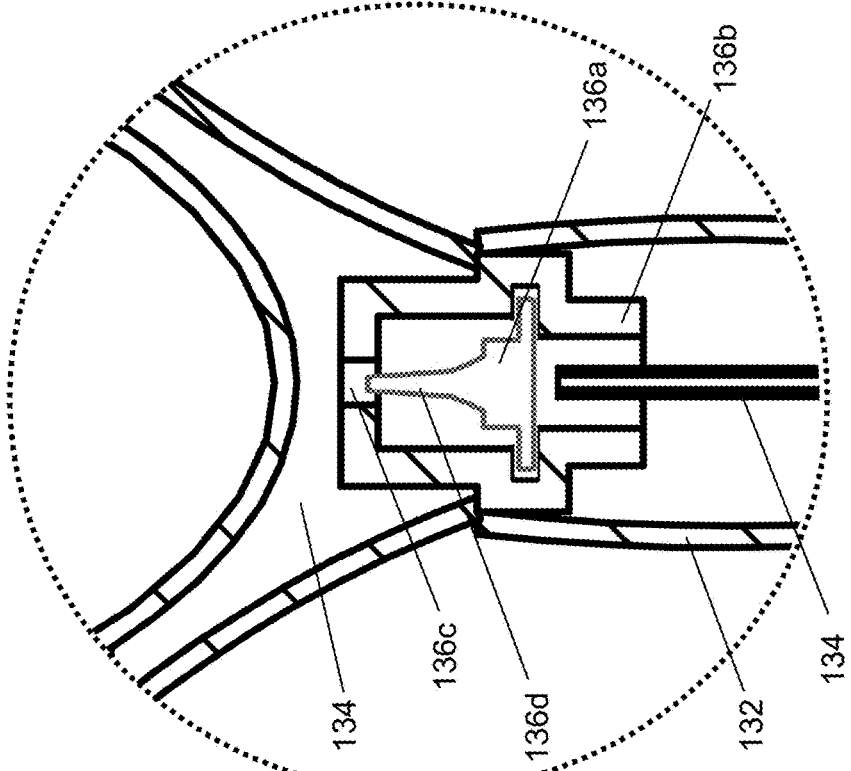

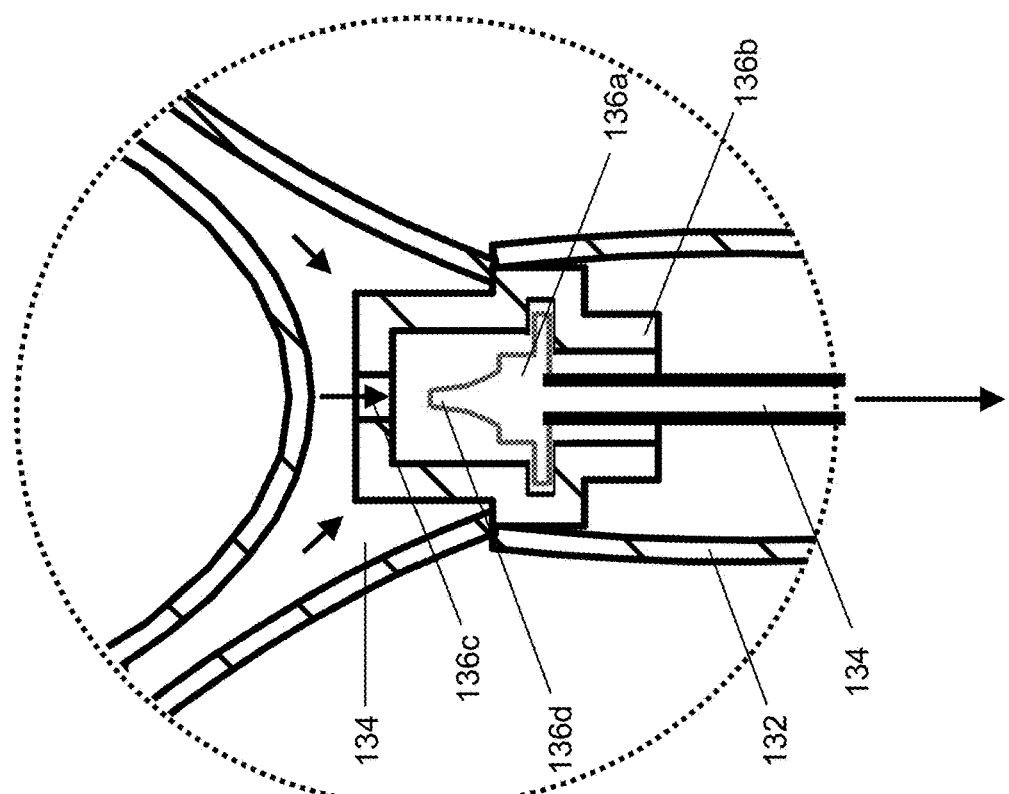
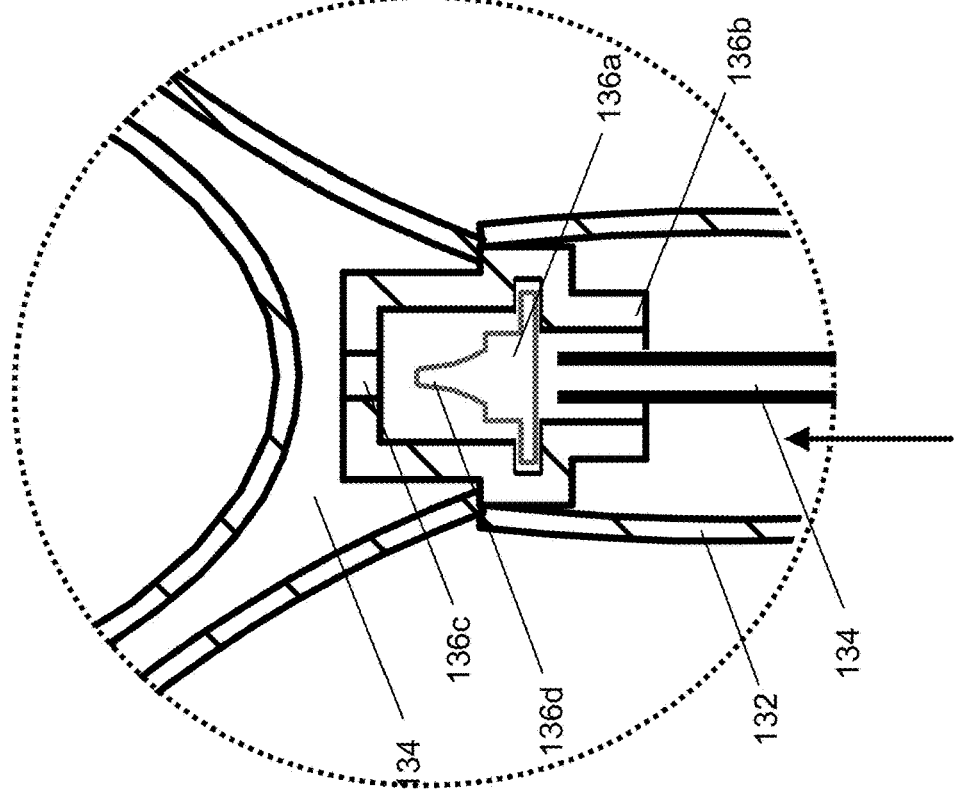

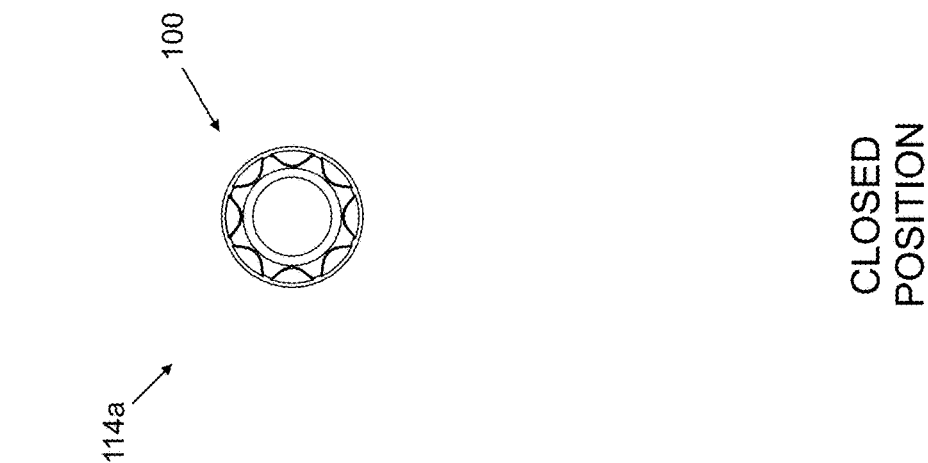
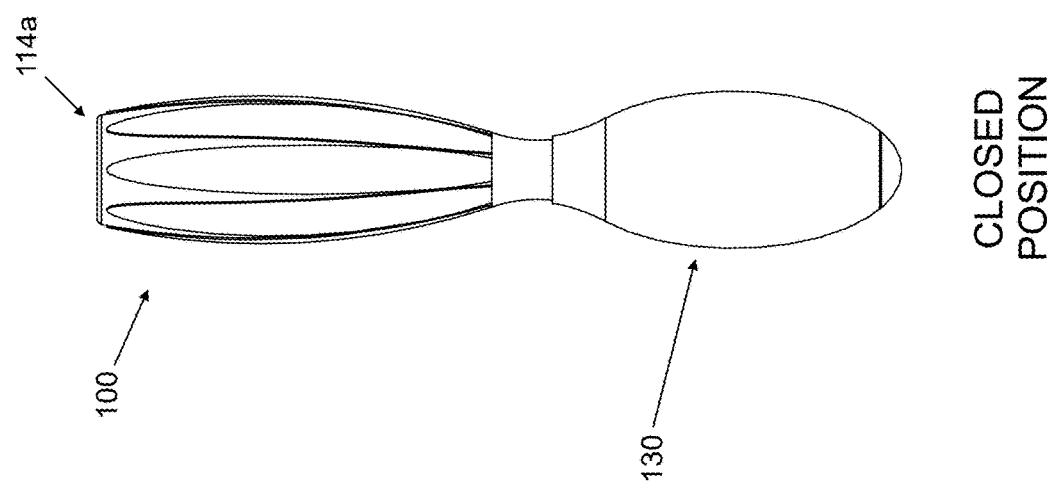

OPEN POSITION

OPEN POSITION

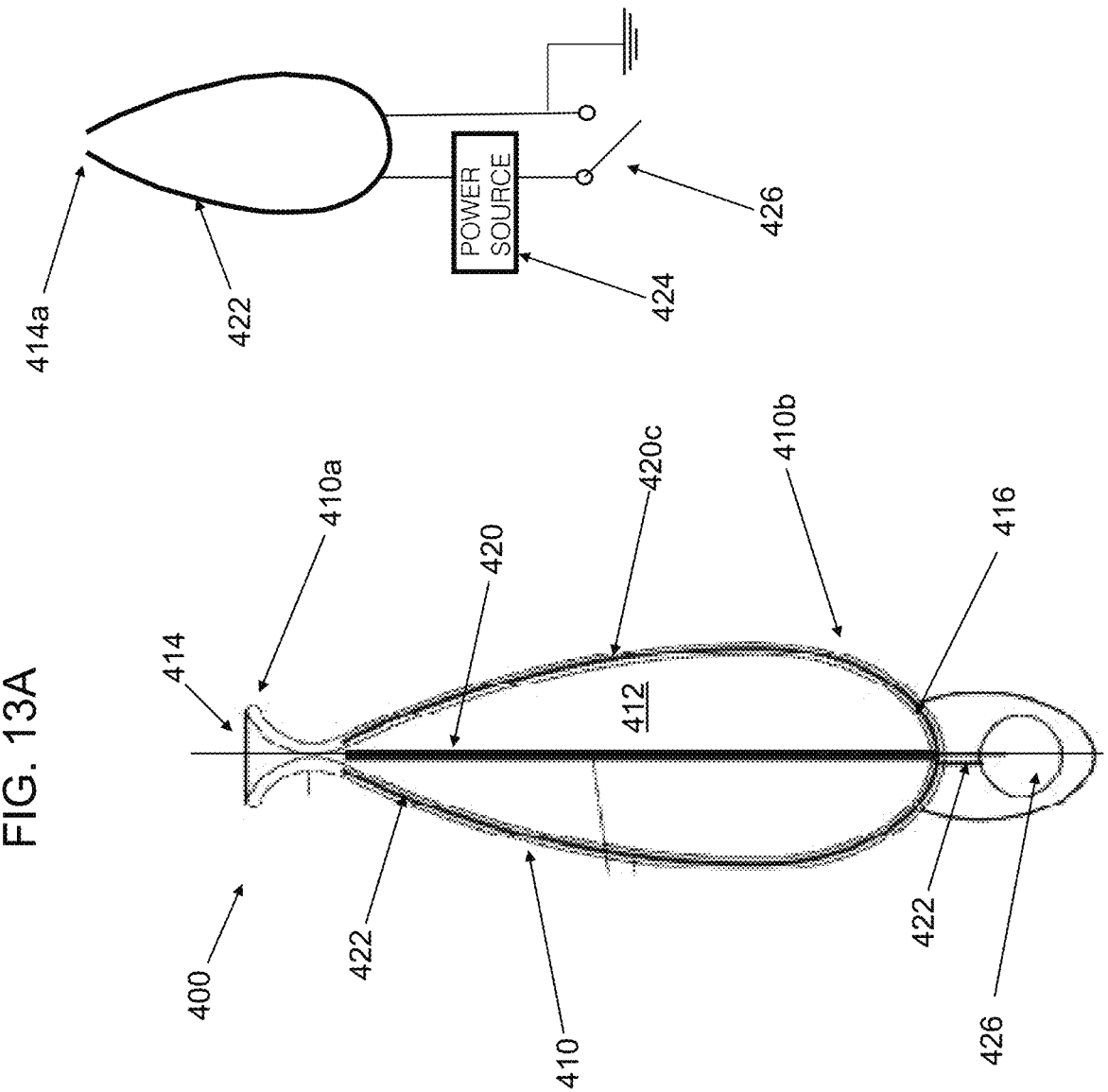

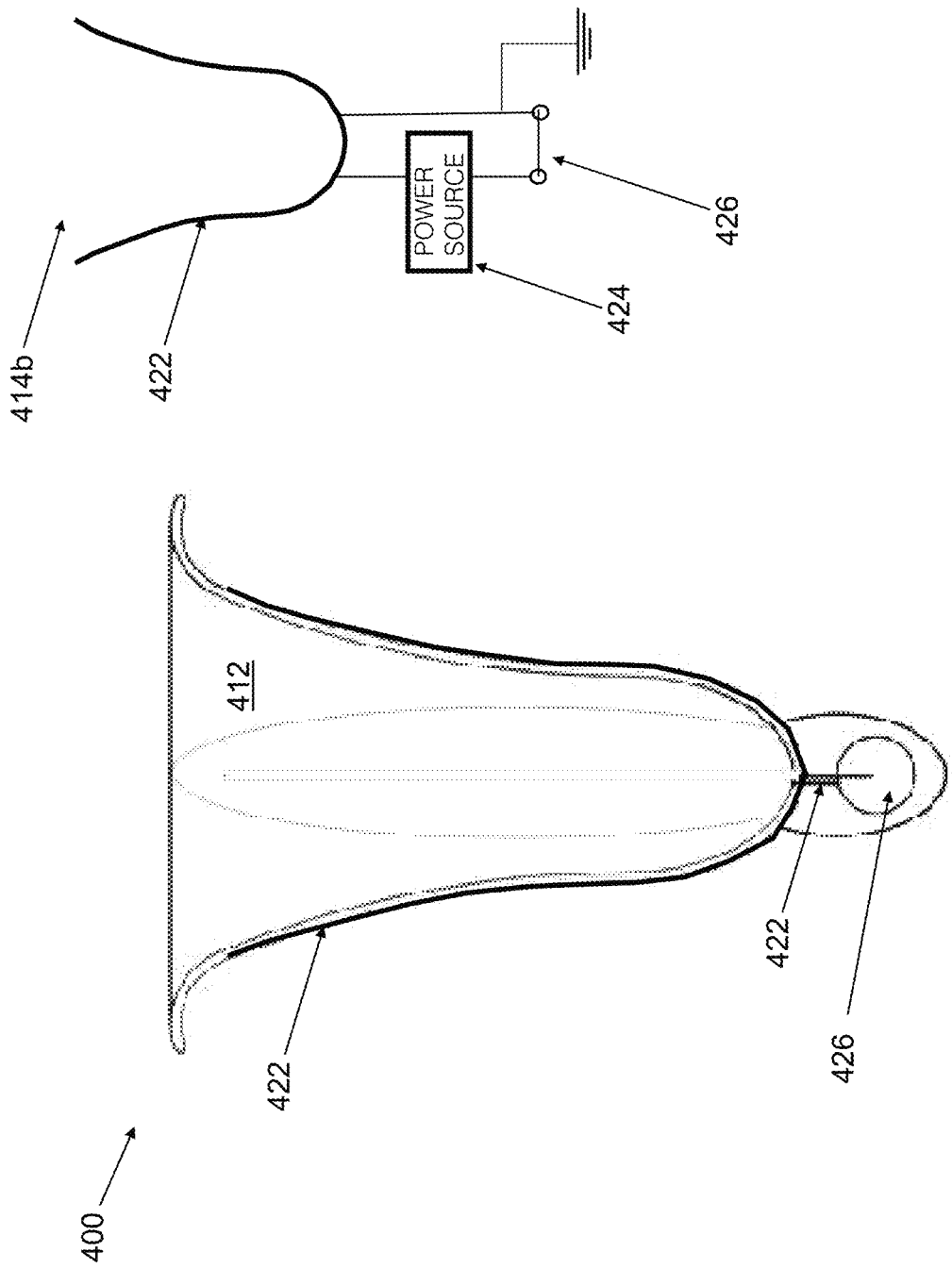

though the embodiments of the present general inventive
MENSTRUAL FLUID COLLECTION DEVICE AND METHOD THEREOF

FIELD OF INVENTION

The present general inventive concept relates to a menstrual cup, and more particularly to a menstrual cup formed of a flexible bio-compatible material having a fluid storage cavity to collect and store menstrual fluid that can be opened and closed.

BACKGROUND

The female reproductive system 10 includes a vagina 12 surrounded by a vaginal canal 14, a cervix 16, and a uterus 18. (See FIG. 1) This system 10 regularly undergoes a natural process (referred to as a menstrual cycle) in which blood and mucosal tissue (i.e., menstrual fluid) is discharged from the uterus 18 through the vagina 12 and vaginal canal 14 to prepare the uterus 18 for pregnancy. As such, menstrual fluid flows to the outside through the vaginal canal 14 often soiling the woman's clothing. As a result, various types of menstrual pads and tampons have been developed and used for decades in order to absorb the menstrual fluid and to protect womens clothing.

In addition, there currently exists various types of menstrual cups which are inserted inside of womens vaginas 12 to collect the menstrual fluid. These menstrual cups have a cavity that is used to collect menstrual fluid which needs to be removed and dispose of and cleaned for hygienic purposes. However, since typical menstrual cups have a receiving end that is formed in an open position, women are required to first squeeze the receiving end in order to be able to insert and remove the menstrual cup from the vaginal canal 14. As such, women must reach inside their vaginas 12 in order to manually squeeze the receiving end closed to prevent spilling the collected fluids, which is unsafe, unsanitary, and inconvenient to the user. Also, when released, the receiving end may cause trauma to user's vagina 12 since vaginal canals 14 vary in size and shape. That is, typical menstrual cups are often too large to comfortably fit and be used by many women.

Therefore, what is needed is a menstrual cup that is designed to accommodate a wider range of women and which allows the user to open and close the opening for ease of insertion and disposal of menstrual fluid without causing harm or leakage of menstrual fluids.

SUMMARY OF THE INVENTION

Features and/or utilities of the present general inventive concept may be achieved by providing a menstrual fluid collection device including a flexible container having a storage cavity to store a fluid and a movable opening formed in a closed position at a first end of the flexible container, the storage cavity to receive the fluid when the movable opening is in an open position and an inflatable seal member coupled to and extending around the flexible container, the inflatable seal member configured to move the opening to the open position, when inflated.

The menstrual fluid collection device may further include a pumping member used to selectively inflate the inflatable seal member.

The least one of the flexible container and the inflatable seal member may be formed of an elastomeric material.

The pumping member may include a pump or various other means for generating or pumping a gas or a fluid into the inflatable seal member.

The menstrual fluid collection device may further include a valve member coupled between the pumping member and the inflatable seal member which is used to control an amount of gas or fluid disposed within the inflatable seal member.

The menstrual fluid collection device may further include a valve control member coupled to the valve member to thereby allow a user to open and close the movable opening of the flexible container by controlling an amount of gas or fluid disposed within the inflatable seal member.

The menstrual fluid collection device may further include a protrusion formed on an outer surface of the inflatable seal member configured to create a seal within a user's vagina.

The valve member may be a one-way valve configured to allow gas and/or a fluid to flow in a single direction.

Features and/or utilities of the present general inventive concept may also be achieved by providing a method for using a menstrual fluid collection device, the device includes a flexible container having a storage cavity to store a fluid and a movable opening formed in a closed position at a first end of the flexible container, the storage cavity to receive the fluid when the movable opening is in an open position and an inflatable seal member coupled to and extending around the flexible container, the inflatable seal member configured to move the opening to the open position, when inflated, the method includes inserting the first end of the flexible container into a user's vagina, inflating the inflatable seal member with a gas to open the movable opening, allowing menstrual fluid to flow into the storage cavity, releasing the gas within the inflatable seal member to allow the movable opening to return to the closed position, and removing the flexible container from the user's vagina.

Additional aspects of the present general inventive concept will be set forth in part in the description which follows and, in part, will be obvious from the description, or may be learned by practice of the general inventive concept.

BRIEF DESCRIPTION OF THE DRAWINGS

These and/or other aspects of the present general inventive concept will become apparent and more readily appreciated from the following description of the embodiments, taken in conjunction with the accompanying drawings of which:

FIG. 7A is an enlarged detail view of section C of the menstrual fluid collection device illustrated in FIG. 4;

FIG. 7B is an enlarged detail view of section D of the menstrual fluid collection device illustrated in FIG. 6;

FIGS. 8A and 8B are enlarged detail cross-sectional views of a one-way valve and release valve according to an exemplary embodiment of the present general inventive concept;

FIG. 9A is a front view of the menstrual fluid collection device illustrated in FIG. 2, in the closed position;

FIG. 9B is a top view of the menstrual fluid collection device illustrated in FIG. 2, in the closed position;

FIG. 13A is a front perspective view of a menstrual fluid collection device according to another exemplary embodiment of the present general inventive concept, in a closed position; and FIG. 13B is a front perspective view of the menstrual fluid collection device illustrated in FIG. 12A, in an open position.

DETAILED DESCRIPTION OF THE INVENTION

Figure 1:
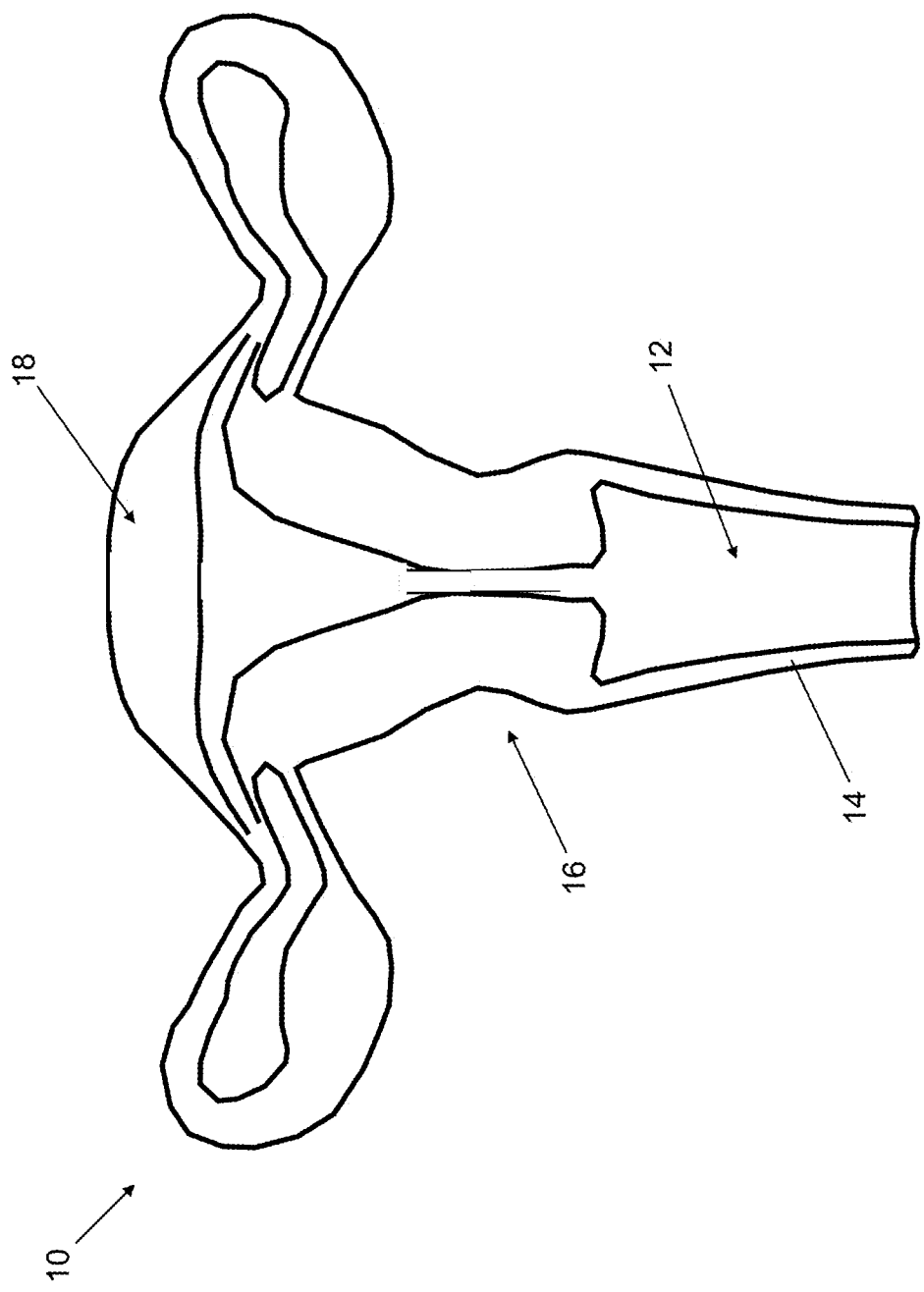
FIG. 1 is a schematic view of a female reproductive system.

Reference will now be made in detail to the exemplary embodiments of the present general inventive concept, examples of which are illustrated in the accompanying drawings, wherein like reference numerals refer to the like elements throughout. The exemplary embodiments are described below in order to explain the present general inventive concept by referring to the figures.

Figure 2:
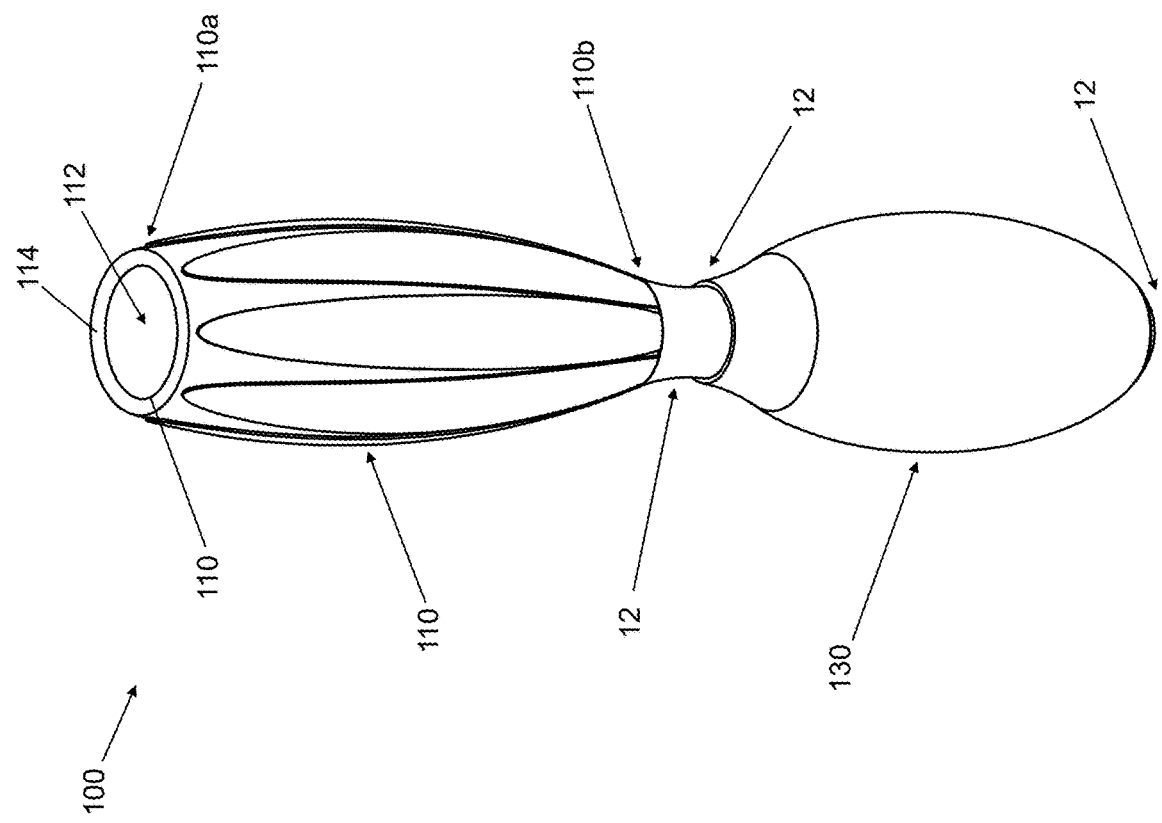
FIG. 2 is a front perspective view of a menstrual fluid collection device according to an exemplary embodiment of the present general inventive concept, in a closed position.
Figure 3:
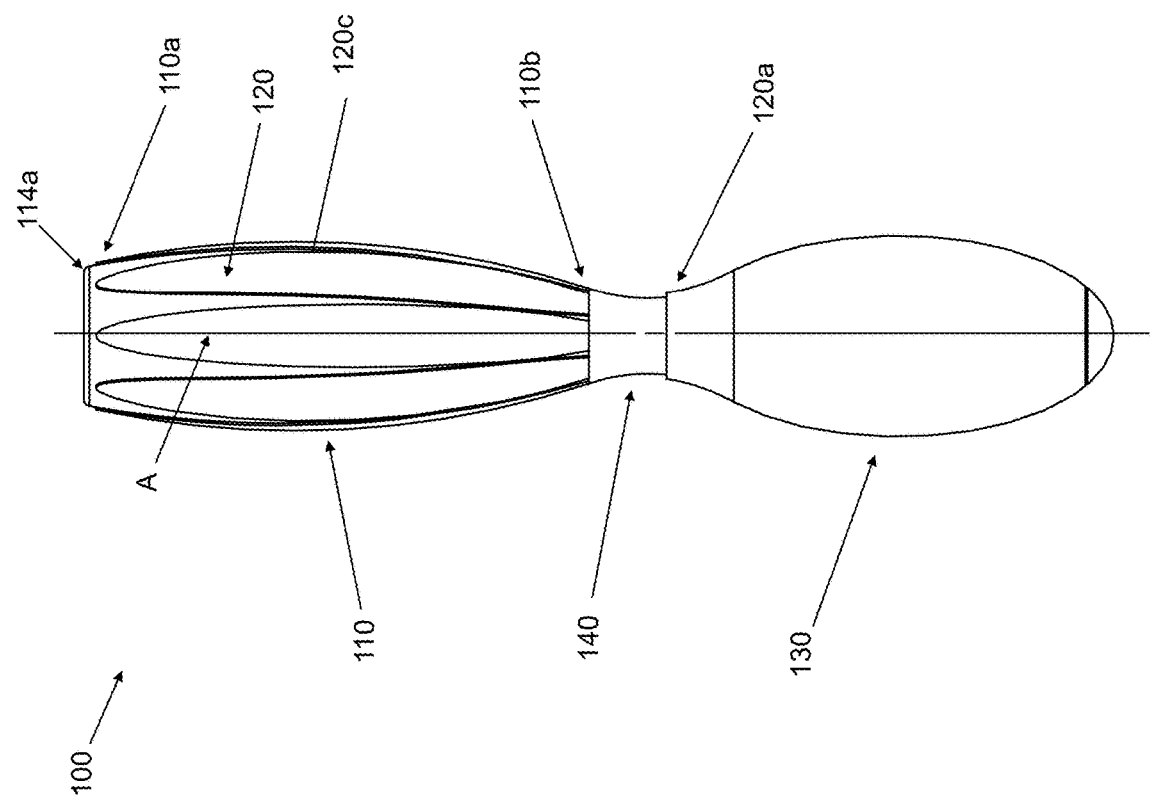
FIG. 3 is a front view of the menstrual fluid collection device illustrated in FIG. 2.
Figure 4:
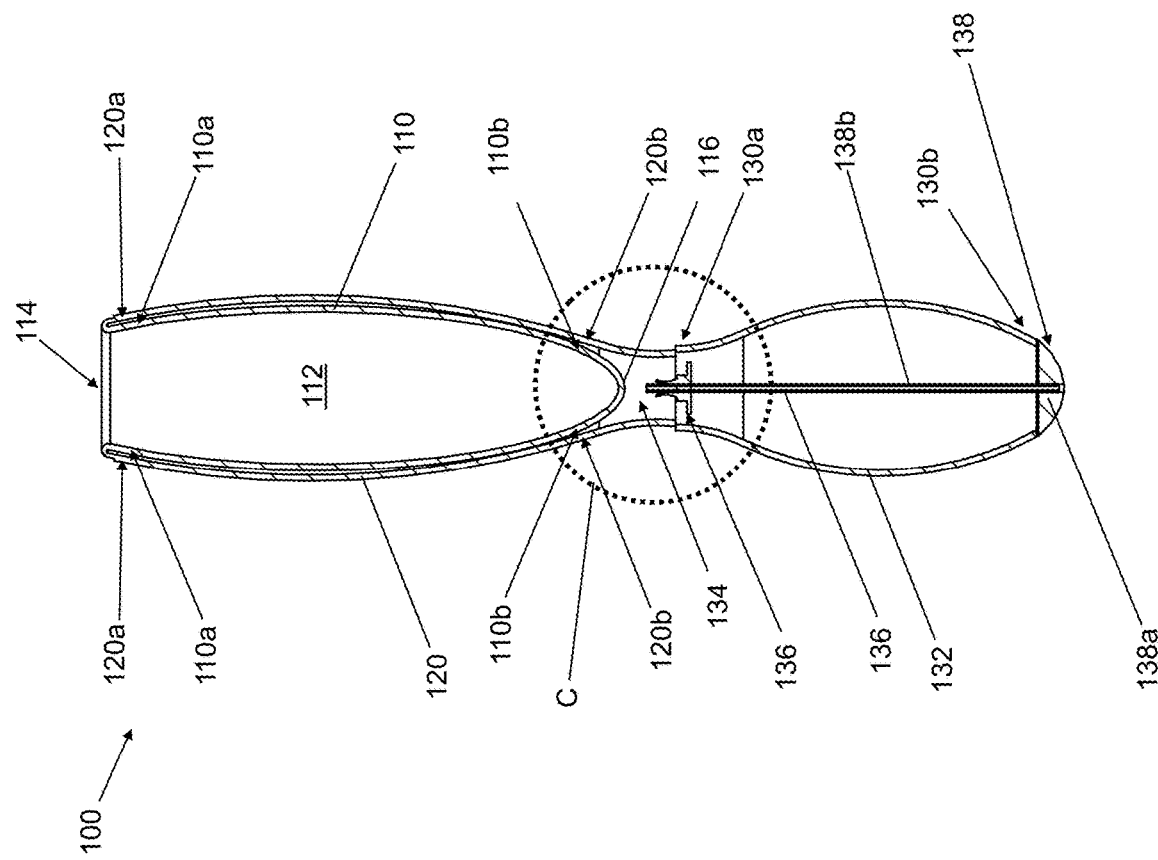
FIG. 4 is a cross-sectional view of the menstrual fluid collection device illustrated in FIG. 3, along line A.
Figure 5:
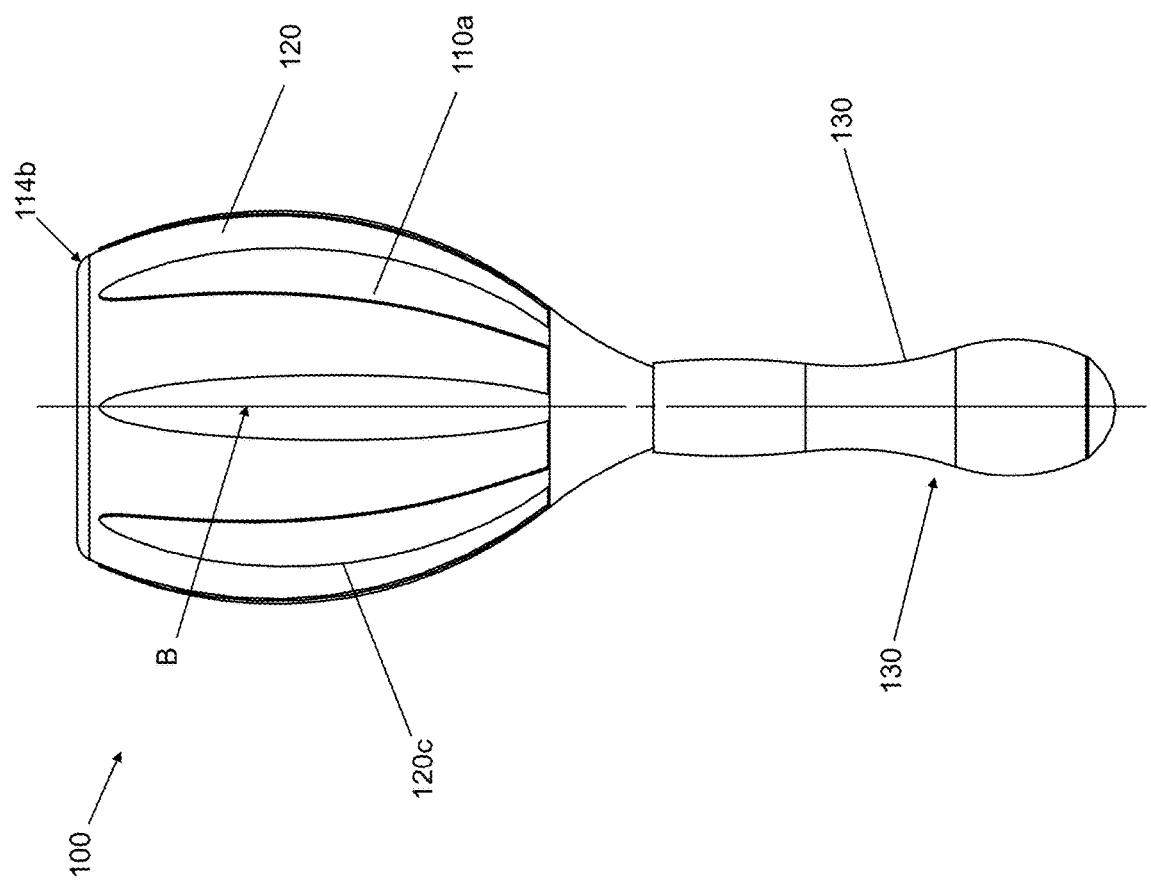
FIG. 5 is a front view of the menstrual fluid collection device illustrated in FIG. 2, in an open position.
Figure 6:
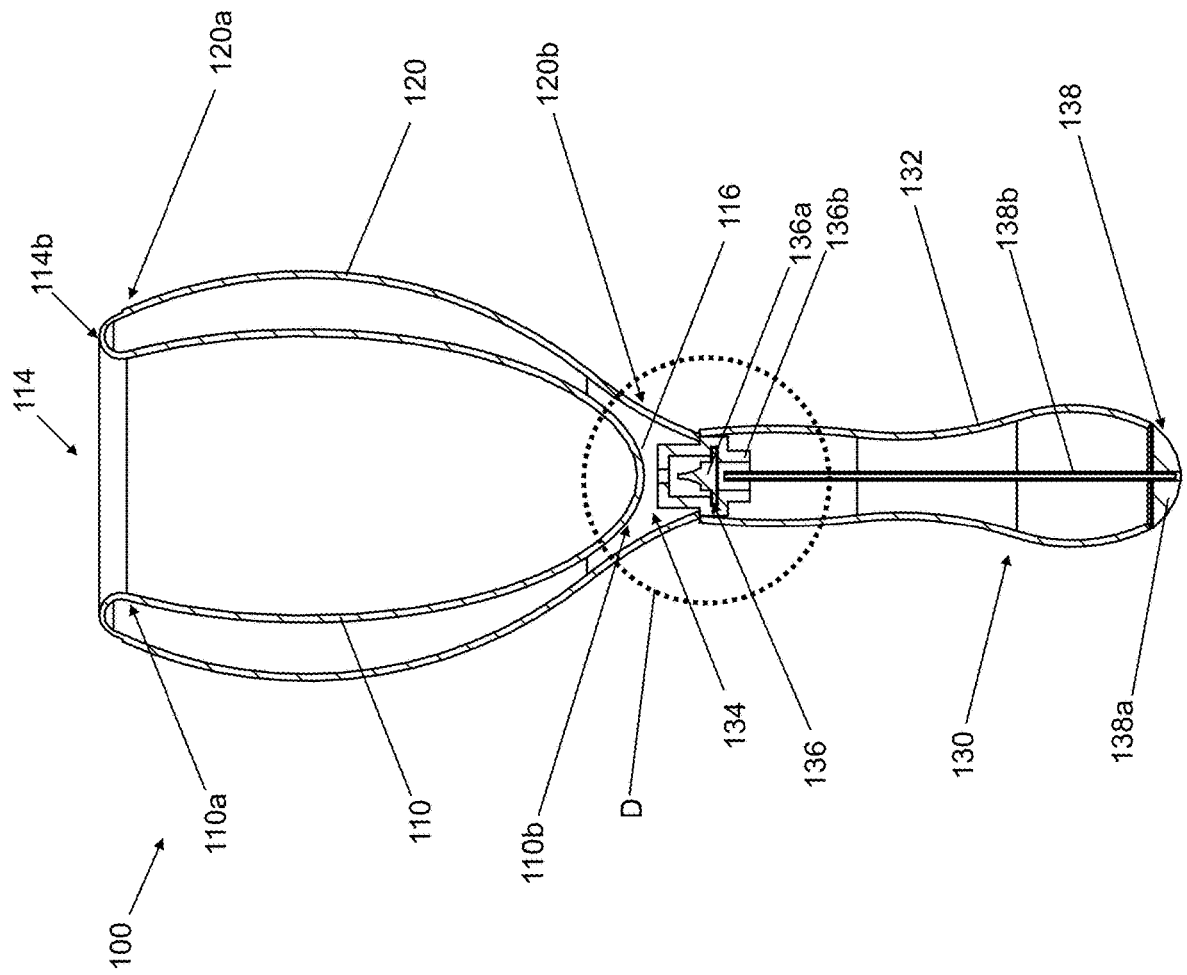
FIG. 6 is a cross-sectional view of the menstrual fluid collection device illustrated in FIG. 5, along line B.

FIG. 2 is a front perspective view of a menstrual fluid collection device 100 according to an exemplary embodiment of the present general inventive concept, in a closed position 114a. FIG. 3 is a front view of the menstrual fluid collection device 100 illustrated in FIG. 2, a closed position 114a. FIG. 4 is a cross-sectional view of the menstrual fluid collection device 100 illustrated in FIG. 3, along line A and FIG. 5 is a front view of the menstrual fluid collection device 100 illustrated in FIG. 2, in an open position 114b. FIG. 6 is a cross-sectional view of the menstrual fluid collection device 100 illustrated in FIG. 5, along line B.

Referring to FIGS. 2 through 6, according to an exemplary embodiment of the present general inventive concept, the menstrual fluid collection device 100 includes a flexible container 110 having a storage cavity 112 defined between a movable opening 114 at a first end 110a and a sealed portion 116 at a second end 110b which is used to collect and store menstrual fluid, an inflatable seal member 120 coupled to and extending around the first end 110a of the flexible container 110 and configured to move the opening 114 from a first position 114a (e.g., a closed position) to a second position 114b (e.g., an open position) when inflated, and a pumping member 130 configured to inflate the inflatable seal member 120 with a gas or fluid to thereby open and close the opening 114 of the flexible container 110. In addition, an outer surface 120c of the inflatable seal member 120 is designed and/or configured to fit and seal within a vaginal canal 12 of a woman's vagina 14 up to a cervix 16 such that menstrual fluid is only allowed to enter the storage cavity 112 of flexible container 110, through the opening 114. In the present embodiment, the movable opening 114 of the flexible container 110 may be used to receive a fluid (e.g., menstrual fluid) from within a female's reproductive system 10 which is then collected within the storage cavity 112 for later disposal.

In exemplary embodiments, the flexible container 110 and the inflatable seal member 120 may be constructed from various elastomeric, bio-compatible materials and formed in various cup-like shapes. The inflatable seal member 120 may be formed into various shapes and sizes in order to be detachably secured within a vaginal canal 14 of a user's vagina 12. However, the present general inventive concept is not limited thereto. That is, in alternative embodiments, the flexible container 110 and the inflatable seal member 120 may be construed from various materials and shapes, as desired.

In the present embodiment, the flexible container 110 may be formed in a closed or partially-closed position of a material having a first durometer D1 and the inflatable seal member 120 may be formed from a material having a second durometer D2. In the present embodiment, the first durometer D1 may be larger than the second durometer D1, such that the opening 114 of the flexible container 110 may be biased toward the closed position 114a (or partially closed) in order to prevent or reduce spillage of the menstrual fluid collected within the storage cavity 112.

In the present embodiment, a first end 120a of the inflatable seal member 120 is coupled to the movable opening 114 at the first end 110a of the flexible container 110, and a second end 120b of the inflatable seal member 120 is coupled to a first end 130a of the pumping member 130. The flexible container 110 may be constructed from a material which has sufficient elasticity to allow the opening 114 to move between the open and closed positions 114a and 114b.

In exemplary embodiments, the pumping member 130 may include a manual or automatic pump that may be used to inflate the inflatable seal member 120 to thereby move the opening 114 from the closed position 114a to the open position 114b. As such, by manually or automatically pumping air (or fluid) into the inflatable seal member 120 by using the pumping member 130, the user may control the opening and closing of the flexible container 110 to insert and prevent or reduce leakage of fluid stored within the storage cavity 112. When inflated, the outer surface 120c of the inflatable seal member 120 may be designed and/or configured to be removably secured within the user's vaginal canal 14, while creating a seal within the user to prevent leakage of fluid from the user's vagina 12 to the outside. When deflated, the flexible container 110 contracts which allows the menstrual fluid collection device 100 to be inserted and removed from within the vaginal canal 12.

FIG. 7A is an enlarged detail view of section C of the menstrual fluid collection device 100 illustrated in FIG. 4. FIG. 7B is an enlarged detail view of section D of the menstrual fluid collection device 100 illustrated in FIG. 6. FIGS. 8A and 8B are enlarged detail cross-sectional views of a one-way valve 136 and release valve 138 according to an exemplary embodiment of the present general inventive concept.

Referring to FIGS. 7A and 7B, in the present embodiment, the pumping member 130 includes a pump bulb 132 which generates or pumps air into a filling chamber 134 through a one-way valve 136 which is disposed in between the pump bulb 132 and the filing chamber 134. In exemplary embodiments, the one-way valve 136 includes an elastic valve member 136a disposed within a valve housing 136b, an inlet port 136c, and a release valve 138 having an outlet port accessible to an exterior of the pump bulb 132. The release valve 138 is movably coupled to the elastic valve member 136a.

As such, when the pump bulb 132 is depressed (inward direction), air disposed within the pump bulb 132 is forced into the filling chamber 134 through the one-way valve 136. Thus, when the pump bulb 132 is depressed, the one-way valve 136 opens as a tip 136d of the elastic member 136a extends into the inlet port 136c thereby allowing air to travel into the filling chamber 134. When the pump bulb 132 is released, the one-way valve 136 closes when the elastic member 136a returns away from the inlet port 136 thereby preventing air to travel into or out of the filling chamber 134. As the filling chamber 134 is inflated, the inflatable seal member 120 is inflated thereby opening the opening 114 of the flexible container 110.

In other words, when a gas or fluid is generated and/or pumped into the filling chamber 134 located in between the flexible container 110 and the inflatable seal member 120, the inflatable seal member 120 inflates (i.e., expands) which forces or pulls the movable opening 114 toward the open position 114b. Conversely, when a gas or fluid is released from the filling chamber 134, the inflatable seal member 120 deflates (i.e., contracts) which forces or pushes the movable opening 114 toward the closed position 114a.

Figure 10B:
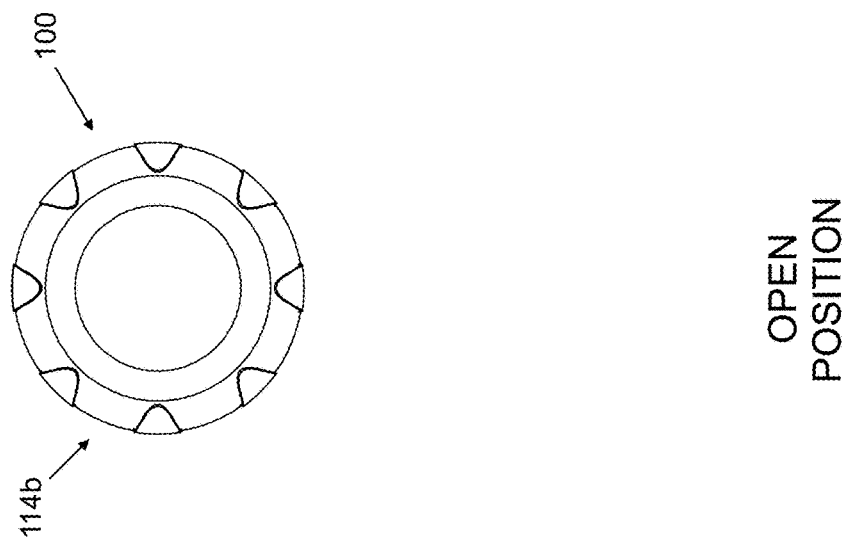
FIG. 10B is a top view of the menstrual fluid collection device illustrated in FIG. 2, in the open position.
Figure 10A:
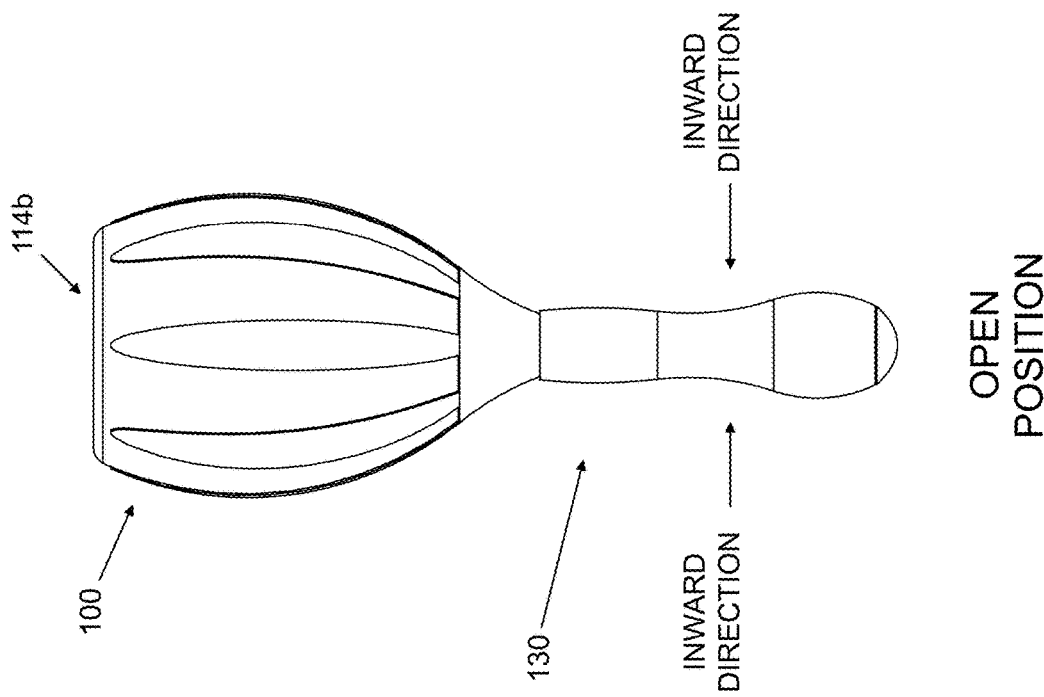
FIG. 10A is a front view of the menstrual fluid collection device illustrated in FIG. 2, in the open position.

FIG. 9A is a front view of the menstrual fluid collection device 100 illustrated in FIG. 2, in the closed position 114a and FIG. 9B is a top view of the menstrual fluid collection device 100 illustrated in FIG. 2, in the closed position 114a. FIG. 10A is a front view of the menstrual fluid collection device 100 illustrated in FIG. 2, in the open position 114b and FIG. 10B is a top view of the menstrual fluid collection device 100 illustrated in FIG. 2, in the open position 114b.

In exemplary embodiments, the release valve 138 includes a gas release button 138a coupled to an outer surface of the pumping member 130 and a gas release channel 138b disposed within the pumping member 130. As such, when the gas release button 138a is pressed, the gas release channel 138b is moved upward into the elastic valve member 136a thereby pushing the tip 136d of the elastic member 136a into the inlet port 136c thereby allowing air to release from the filling chamber 134 to the outside through the gas release channel 138b and the gas release button 138a. As such, by pressing the gas release button 138a, the opening 114 is moved from the open position 114b to the closed position 114a.

Figure 11A:
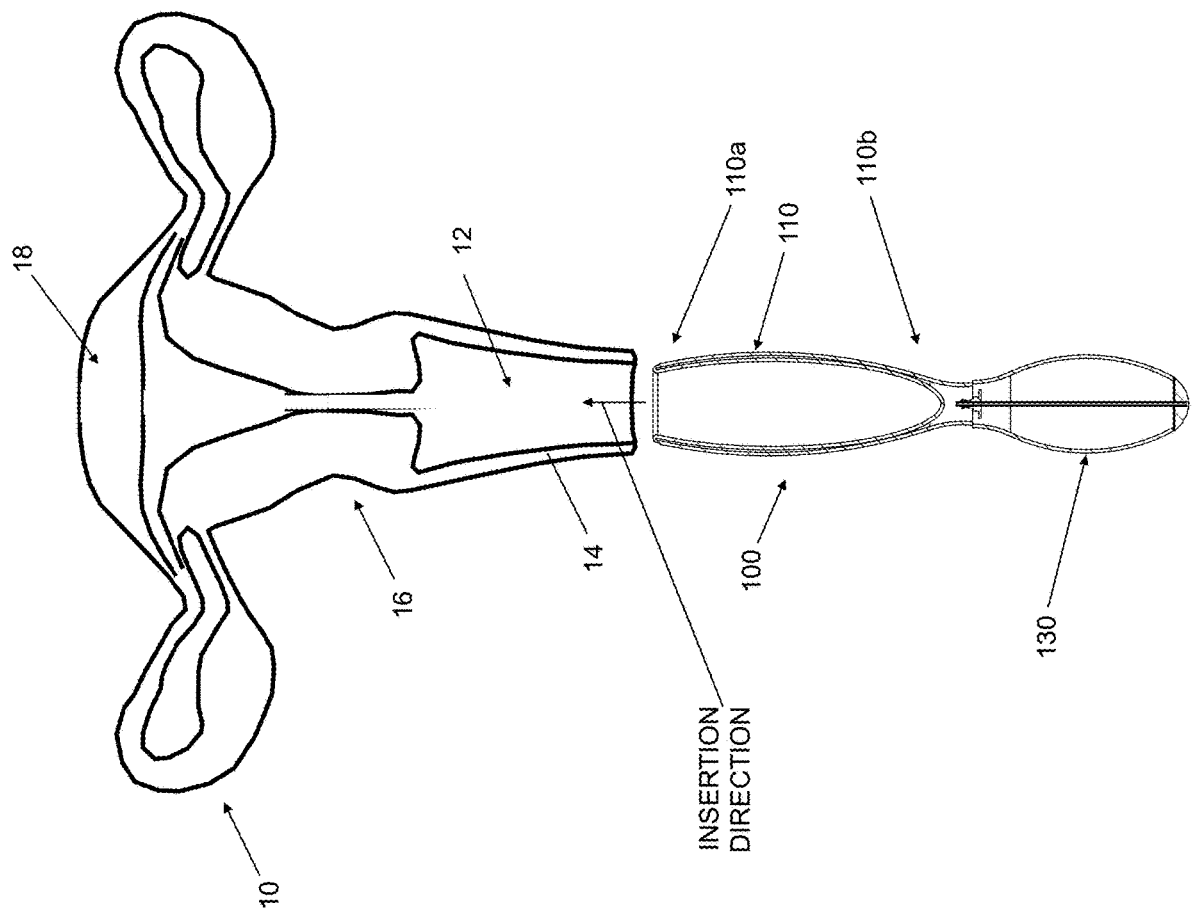
FIGS. 11A through 11C illustrate a cross-sectional view of a method of using the menstrual fluid collection device illustrated in FIG. 2, according to an exemplary embodiment of the present general inventive concept.
Figure 11B:
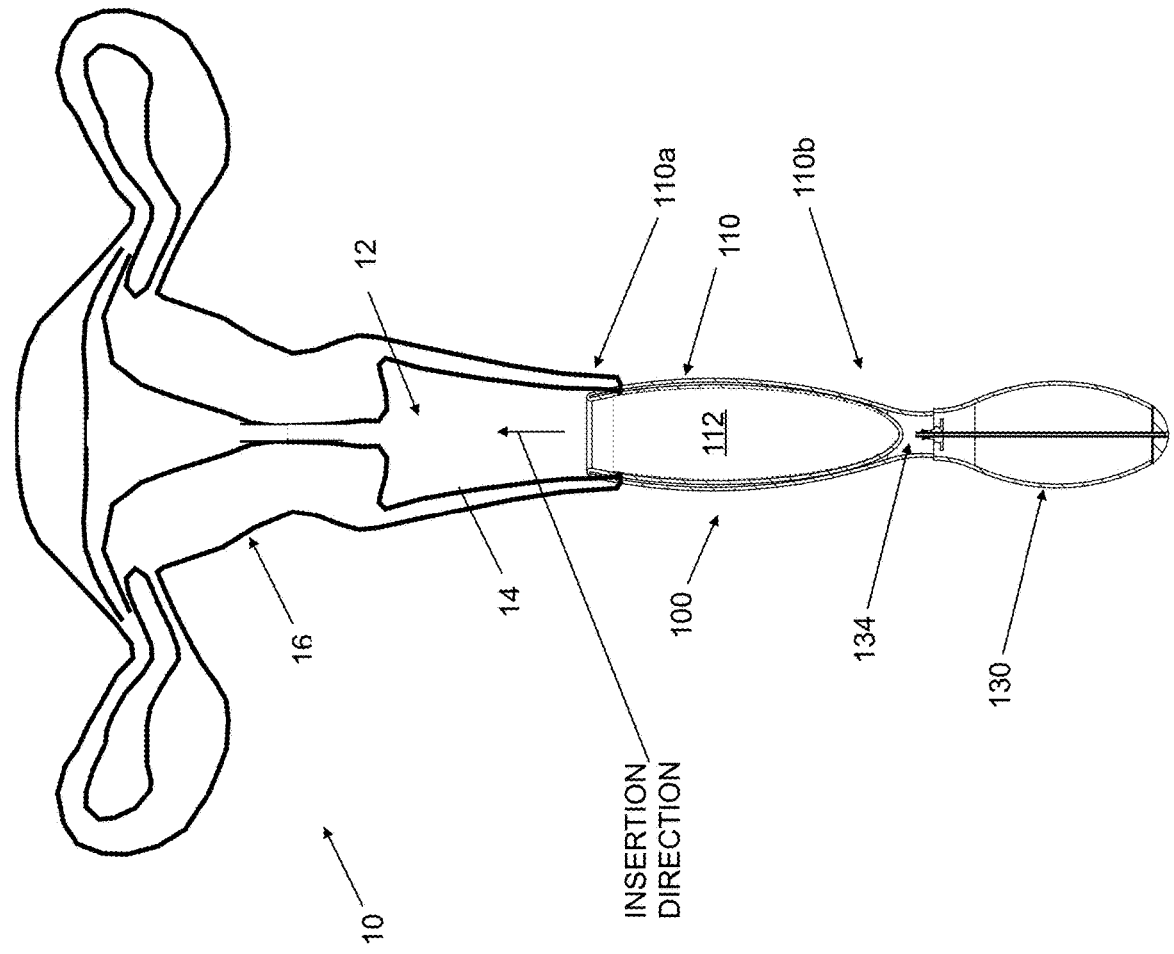
Figure 11C:
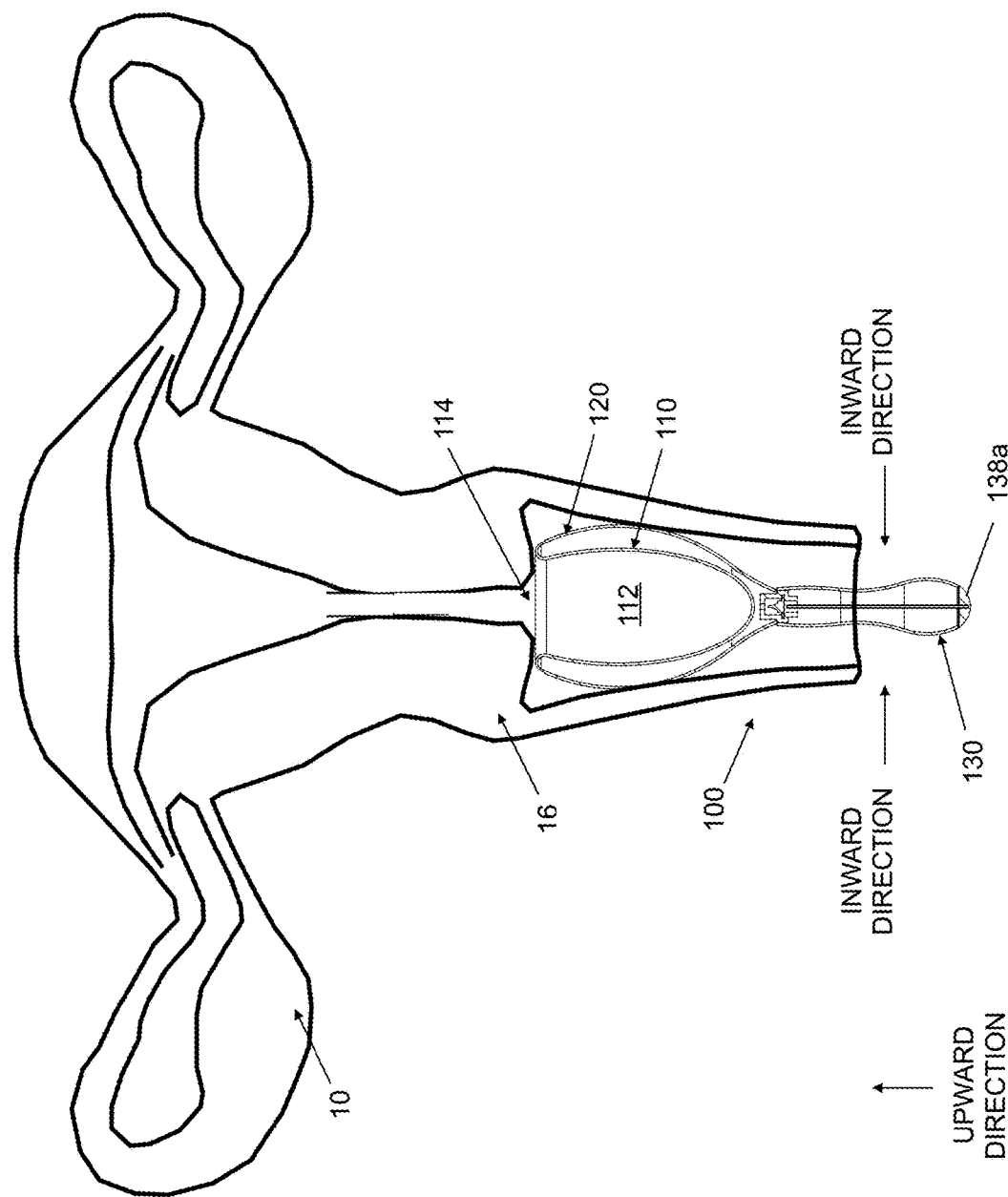

FIGS. 11A through 11C illustrate a cross-sectional view of a method 200 of using the menstrual fluid collection device 100 illustrated in FIG. 2, according to an exemplary embodiment of the present general inventive concept.

An exemplary embodiment method 200 of using the menstrual fluid collection device 100 according to the present general inventive concept includes obtaining a menstrual fluid collection device 100, inserting a first end 110a of the flexible container 110 into a user's vagina 12 up to or adjacent to the user's cervix 16, using the pumping member 130 to inflate the inflatable seal member 120 to move the opening 114 to the open position 114b, allowing the flexible container 110 to receive, collect, and store menstrual fluid originating from within the user, pressing the gas release button 138a in the upward direction to release the gas disposed within the filling chamber 134 to outside of the pumping member 130 which, in turn, moves the opening 114 from the open position 114b to the closed position 114a.

Figure 12B:
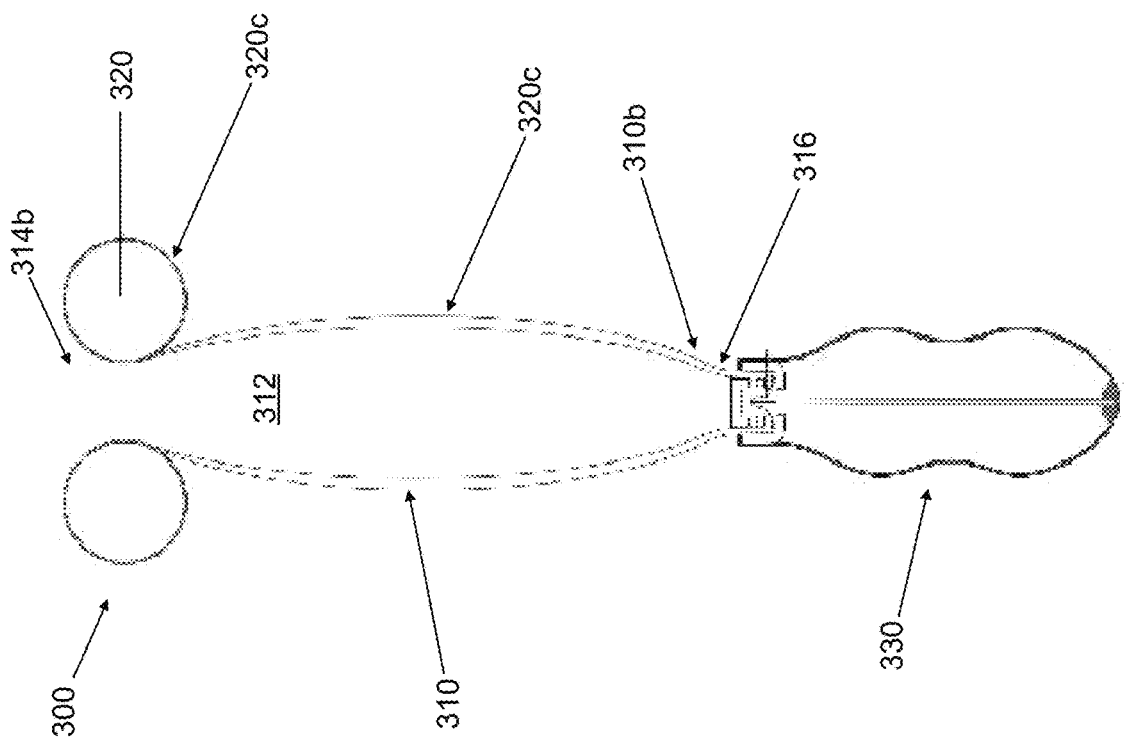
FIG. 12B is a front view of the menstrual fluid collection device illustrated in FIG. 12A, in an open position.
Figure 12A:
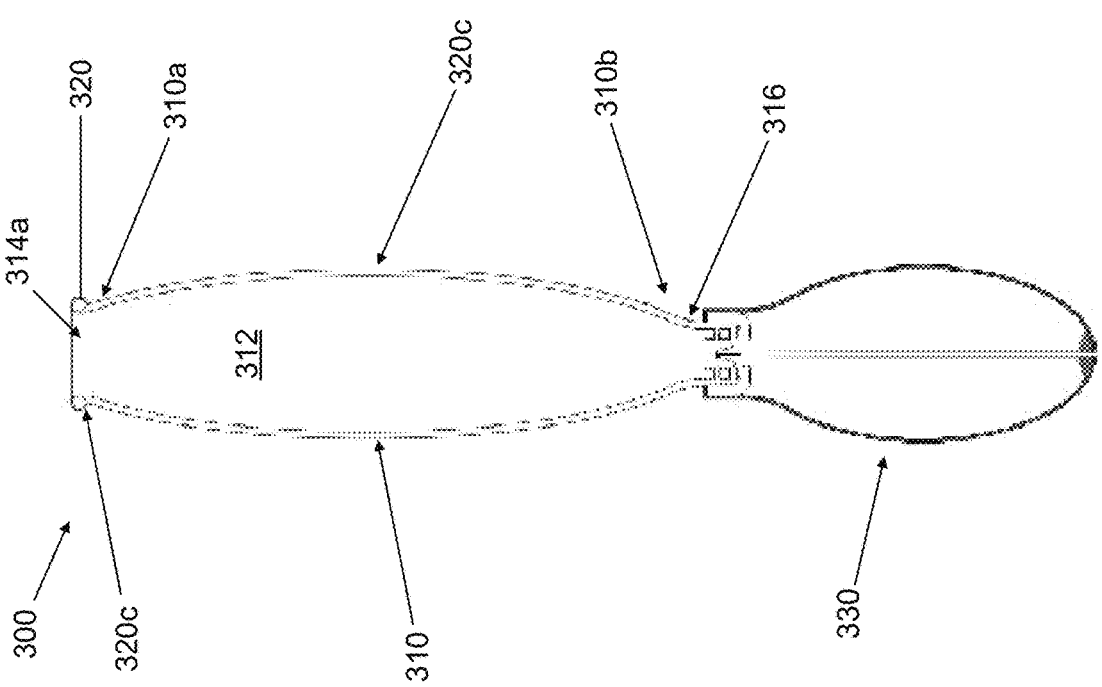
FIG. 12A is a front view of a menstrual fluid collection device according to another exemplary embodiment of the present general inventive concept, in a closed position.

FIG. 12A is a front view of a menstrual fluid collection device 300 according to another exemplary embodiment of the present general inventive concept, in a closed position and FIG. 12B is a front view of the menstrual fluid collection device 300 illustrated in FIG. 12A, in an open position.

The present exemplary embodiment is similar to the previous embodiments except the inflatable seal member 320 is formed in a ring shape which may be inflated to open and close the flexible container 310 by using the pumping member 330. However, the present general inventive concept is not limited thereto. That is, in alternative embodiments, the inflatable seal member 320 may be formed in various shapes and sizes including disc-shaped and doughnut shaped.

In the present embodiment, the menstrual fluid collection device 300 includes a flexible container 310 having a storage cavity 312 defined between a movable opening 314 at a first end 310a and a sealed portion 316 at a second end 310b which is used to collect and store menstrual fluid, an inflatable seal member 320 coupled to and extending around the first end 310a of the flexible container 310 and configured to move the opening 314 from a first position 314a (e.g., a closed position) to a second position 314b (e.g., an open position) when inflated, and a pumping member 330 configured to inflate the inflatable seal member 320 with a gas or fluid to thereby open and close the opening 314 of the flexible container 310. In addition, an outer surface 320c of the inflatable seal member 120 is designed and/or configured to fit and seal within a vaginal canal 12 of a woman's vagina 14 up to a cervix 16 such that menstrual fluid is only allowed to enter the storage cavity 312 of flexible container 310, through the opening 314. In the present embodiment, the movable opening 314 of the flexible container 310 may be used to receive a fluid (e.g., menstrual fluid) from within a female's reproductive system 10 which is then collected within the storage cavity 312 for later disposal.

FIG. 13A is a front perspective view of a menstrual fluid collection device 400 according to another exemplary embodiment of the present general inventive concept, in a closed position and FIG. 13B is a front perspective view of the menstrual fluid collection device 400 illustrated in FIG. 13A, in an open position.

The present exemplary embodiment is similar to the previous embodiments and further includes a shape memory alloy frame which may be used to open and close the opening 414 by using a power source (battery).

The menstrual fluid collection device 400 includes a flexible container 410 having a storage cavity 412 defined between a movable opening 414 at a first end 410a and a sealed portion 416 at a second end 410b which is used to collect and store menstrual fluid, an expandable seal member 420 consisting of a shape memory alloy 422 coupled to and extending within the flexible container 410 and configured to move the opening 414 from a first position 414a (e.g., a closed position) to a second position 414b (e.g., an open position) when activated. Thereby allowing a user to open and close the opening 414 of the flexible container 410 by completing a circuit including a battery 424 using a button 426.

In addition, an outer surface 420c of the inflatable seal member 420 is designed and/or configured to fit and seal within a vaginal canal 12 of a woman's vagina 14 up to a cervix 16 such that menstrual fluid is only allowed to enter the storage cavity 412 of flexible container 410, through the opening 414. In the present embodiment, the movable opening 414 of the flexible container 410 may be used to receive a fluid (e.g., menstrual fluid) from within a female's reproductive system 10 which is then collected within the storage cavity 412 for later disposal.

Although a few exemplary embodiments of the present general inventive concept have been illustrated and described, it will be appreciated by those skilled in the art that changes may be made in these exemplary embodiments without departing from the principles and spirit of the general inventive concept, the scope of which is defined in the appended claims and their equivalents.

What is claimed is:

1. A menstrual fluid collection device comprising:
    a flexible container having a double wall formed from a single sheet having a first durometer including an outer wall and an inner wall and a storage cavity to store a fluid and a movable opening formed in a closed position at a first end of the flexible container, the storage cavity to receive the fluid when the movable opening is in an open position;
    an inflatable seal member coupled to and extending around the flexible container, the inflatable seal member having a second durometer and configured to move the moveable opening to the open position when air is inflated in between the outer and inner wall of the flexible container;
    a pumping member having a pump bulb coupled to the outer wall of the flexible container; and
    a valve member disposed between the outer and inner wall of the flexible container,
    wherein the pumping member is configured to inflate the inflatable seal member through the valve member when depressed and the first durometer is larger than the second durometer so that the movable opening is biased toward the closed position.

2. The menstrual fluid collection device of claim 1, wherein at least one of the flexible container and the inflatable seal member is elastomeric.

3. The menstrual fluid collection device of claim 1, wherein the valve member controls an amount of gas disposed within the inflatable seal member.

4. The menstrual fluid collection device of claim 3, further comprising a valve control member coupled to the valve member to thereby allow a user to open and close the movable opening of the flexible container.

5. The menstrual fluid collection device of claim 4, further comprising a protrusion formed on an outer surface of the inflatable seal member configured to create a seal within a user's vagina.

6. The menstrual fluid collection device of claim 3, wherein the valve member is a one-way valve configured to allow gas to flow in a single direction.

7. A method for using a menstrual fluid collection device, the device comprising a flexible container having a double wall formed from a single sheet having a first durometer including an outer wall and an inner wall and a storage cavity to store a fluid and a movable opening formed in a closed position at a first end of the flexible container, the storage cavity to receive the fluid when the movable opening is in an open position, an inflatable seal member coupled to and extending around the flexible container, the inflatable seal member having a second durometer and configured to move the movable opening to the open position when air is inflated in between the outer and inner wall, a pumping member having a pump bulb coupled to the outer wall of the flexible container and a valve member disposed between the outer and inner wall of the flexible container, wherein the pumping member is configured to inflate the inflatable seal member through the valve member when depressed and the first durometer is larger than the second durometer so that the movable opening is biased toward the closed position, the method comprising:
    inserting the first end of the flexible container into a user's vagina;
    inflating the inflatable seal member with a gas by depressing the pumping member to open the movable opening;
    allowing menstrual fluid to flow into the storage cavity;
    releasing the gas within the inflatable seal member to allow the movable opening to return to the closed position; and
    removing the flexible container from the user's vagina.

8. The method of claim 7, wherein the pumping member selectively inflates the inflatable seal member.

9. The method of claim 7, wherein at least one of the flexible container and the inflatable seal member is elastomeric.

10. The method of claim 9, wherein the pumping member includes at least one of a manual air pump bulb and an automatic air pump.

11. The method of claim 8, wherein the valve member is coupled between the pumping member and the inflatable seal member to control an amount of gas disposed within the inflatable seal member.

12. The method of claim 11, further comprising a valve control member coupled to the valve member to thereby allow a user to open and close the movable opening of the flexible container.

13. The method of claim 9, wherein the pumping member further includes a protrusion formed on an outer surface of the inflatable seal member configured to create a seal within a user's vagina.

14. The method of claim 11, wherein the valve member is a one-way valve configured to allow gas to flow in a single direction.

* * * * *